United States Patent
Peters et al.

(10) Patent No.: US 9,375,444 B2
(45) Date of Patent: Jun. 28, 2016

(54) COMPOSITION FOR PREVENTION AND TREATMENT OF ALLERGIC AND/OR INFLAMMATORY DISEASES

(71) Applicants: PROTECTIMMUN GMBH, Bochum (DE); FORSCHUNGSZENTRUM BORSTEL, Borstel (DE)

(72) Inventors: Marcus Peters, Haltern am See (DE); Marion Kauth, Bochum (DE); Albrecht Bufe, Bochum (DE); Otto Holst, Bad Oldesloe (DE)

(73) Assignees: PROTECTIMMUN GMBH, Bochum (DE); FORSCHUNGSZENTRUM BORSTEL, Borstel (DE)

( * ) Notice: Subject to any disclaimer, the term of this patent is extended or adjusted under 35 U.S.C. 154(b) by 0 days.

(21) Appl. No.: 14/059,180

(22) Filed: Oct. 21, 2013

(65) Prior Publication Data
US 2014/0154290 A1    Jun. 5, 2014

Related U.S. Application Data

(62) Division of application No. 13/059,406, filed as application No. PCT/EP2009/005911 on Aug. 14, 2009, now abandoned.

(30) Foreign Application Priority Data

Aug. 16, 2008 (EP) .................................. 08014587

(51) Int. Cl.
    A61K 31/715    (2006.01)
    A61K 36/899    (2006.01)
    A61K 35/74     (2015.01)
    A61K 35/10     (2015.01)
    A61K 35/744    (2015.01)
    A61K 38/16     (2006.01)

(52) U.S. Cl.
    CPC ............... *A61K 31/715* (2013.01); *A61K 35/10* (2013.01); *A61K 35/74* (2013.01); *A61K 35/744* (2013.01); *A61K 36/899* (2013.01); *A61K 38/168* (2013.01)

(58) Field of Classification Search
    None
    See application file for complete search history.

(56) References Cited

U.S. PATENT DOCUMENTS

| 2004/0185032 A1* | 9/2004 | Burrell .................. A61K 31/135 424/93.45 |
| 2006/0045930 A1* | 3/2006 | Arora ...................... A61K 36/66 424/774 |
| 2008/0206284 A1 | 8/2008 | Williams et al. |

FOREIGN PATENT DOCUMENTS

| DE | 10007771 A | 8/2001 | |
| DE | 20202562 U1 | 6/2002 | |
| DE | 10101793 A | 8/2002 | |
| EP | 0178443 A2 | 4/1986 | |
| EP | 0904784 A1 | 3/1999 | |
| EP | 1538198 A2 | 6/2005 | |
| EP | 1637147 A1 | 3/2006 | |
| EP | 1964570 A1 | 9/2008 | |
| JP | 57009722 A2 | 1/1982 | |
| JP | 10007577 A2 | 1/1998 | |
| JP | 2997774 B2 | 1/2000 | |
| KR | 10-2001-0106068 | 11/2001 | |
| KR | 10-2004-0044300 | 5/2004 | |
| WO | WO 95/31984 A | 11/1995 | |
| WO | WO 96/00579 | 1/1996 | |
| WO | WO 00/16786 A | 3/2000 | |
| WO | WO 01/49319 | * 7/2001 | ............. A61K 39/02 |
| WO | WO 01/49319 A1 | 7/2001 | |
| WO | WO 2005/030230 A | 4/2005 | |
| WO | WO 2006/025068 A | 3/2006 | |

OTHER PUBLICATIONS

Showalter, Cell. Mol. Life Sci. (2001) 58, 1399-1417.*
Su et al., J Biomed Sci (2003) 10, 111-119.*
Kimoto et al., (Microbiol. Immunol. (2004) 48(2) 75-82.*
Gandy, Dissertation for M.S. Pharmacology, (2007), Dept. of Pharmacology, University of Pretoria, available at http://tracebev.com/wp-content/uploads/2013/09/fulvic-acid-dissertation.pdf.*
Strimas et al., Annals of Allergy (1988) 61, 133-136.*
Rajan, Trends in Immunology (2003) 24(7), 376-379.*
Brecker et al., Structural and immunological properties of arabinogalactan polysaccharides from pollen of timothy grass (*Phleum pratense* L.), Carbohydrate Research, 2005, vol. 340, pp. 657-663.
Cocoon Nutrition: "Quantum Adrenal Complex" XP002505224, Dec. 19, 2002.
Cortes-Perez, et al., Intranasal coadministration of live lactococci producing interleukin-12 and a major cow's milk allergen inhibits allergic reaction in mice, Clinical and Vaccine Immunology, Mar. 2007, vol. 14, Issue 3, pp. 226-233.
Currier et al., Effect over time of in-vivo administration of the polysaccharide arabinogalactan on immune and hemopoietic cell lineages in murine spleen and bone marrow, Phytomedicine, 2003, vol. 10, pp. 145-153.

(Continued)

*Primary Examiner* — Marcela M Cordero Garcia
*Assistant Examiner* — Catherine Mader
(74) *Attorney, Agent, or Firm* — Knobbe, Martens, Olson & Bear, LLP

(57) ABSTRACT

A prophylactic antiallergenic composition includes at least one arabinogalactan or arabinogalactan protein. The arabinogalactan or arabinogalactan protein is isolated from a grass or corresponds in its structural arrangement to an arabinogalactan that can be isolated from a grass.

17 Claims, 12 Drawing Sheets

(56) References Cited

OTHER PUBLICATIONS

Figure 1A:
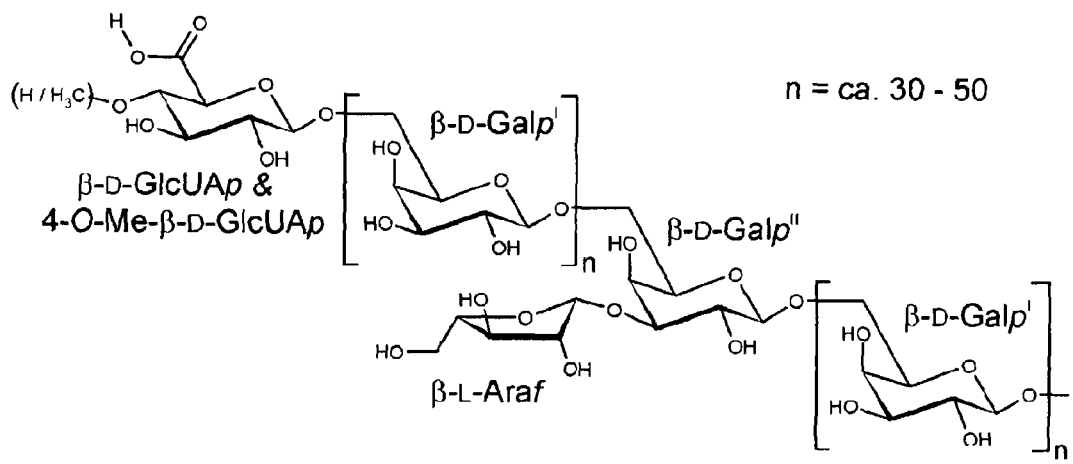

Daniel et al., Modulation of allergic immune responses by mucosal application of recombinant lactic bacteria producing the major birch pollen allergen Bet v 1, Allergy, 2006, vol. 61, pp. 812-819.
Duan et al., Structural features of a pectic arabinogalactan with immunological activity from the leaves of Diospyros kaki, Carbohydrate Research, 2003, vol. 338, pp. 1291-1297.
Franks et al., Variations of bacterial populations in human feces measured by fluorescent in situ hybridization with group-specific 16s rRNA-targeted oligonucleotide probes, Applied and environmental microbiology, Sep. 1998, vol. 64, Issue 9, pp. 3336-3345.
Gandy, An Evaluationof the Anti-Allergic Properties of Potassium Humate, Dissertation (Jan. 2007) University of Pretoria, available at http://upetd.up.ac.za/thesis/available/etd-04292008- 095801/unrestricted/dissertation.pdf.
Huis In't Veld, J.H.J., De rol van melkzuurbacterien bij voeding en gezondheid, Ned Tijdschr Tandheelkd, 1992, vol. 99, pp. 467-471.
International Search Report dated Dec. 18, 2009, for International Application No. PCT/EP2009/005911.
Kelly, G.S., Larch arabinogalactan: Clinical relevance of a novel immune-enhancing polysaccharide, Alternative Medicine Review, 1999, vol. 4, Issue 2, pp. 96-103.
Kim et al., Immunological activity of larch arabinogalactan and echinacea: A preliminary, randomized, double-blind, placebo-controlled trial, Alternative Medicine Review, 2002, vol. 7, Issue 2, pp. 138-149.
Kimoto et al., New lactococcus strain with immunomodulatory activity: Enhancement of Th1-type immune response, Microbiol. Immunol., 2004, vol. 48, Issue 2, pp. 75-82.
Ouwehand, A.E., Antiallergic effects of probiotics, The Journal of Nutrition, 2007, vol. 137, pp. 794S-797S.
Perdigon et al., Influence of the oral administration of lactic acid bacteria on IgA producing cells associated to bronchus, International Journal of Immunopathology and Pharmacology, 1999, vol. 12, Issue 2, pp. 97-102.
Perdigon et al., Study of the possible mechanisms involved in the mucosal immune system activation by lactic acid bacteria, J. Dairy Sci., 1999, vol. 82, Issue 6, pp. 1008-1114.
Taguchi et al., Structure of oligosaccharide side chains of an intestinal immune system modulating arabinogalactan isolated from rhizomes of *Atractylodes lancea* DC, Carbohydrate Research, 2004, vol. 339, pp. 763-770.
Villamil et al., Evaluation of immunomodulatory effects of lactic acid bacteria in turbot (*Scophthalmus maximus*), Clinical and Diagnostic Laboratory Immunology, Nov. 2002, vol. 9, Issue 6, pp. 1318-1323.
Vitini et al., Gut Mucosal immunostimulation by lactic acid bacteria, Biocell, 2000, vol. 24, Issue 3, pp. 223-232.
Wu, C. et al., Immunomodulatory effects of IL-12 secreted by Lactococcus lactis on Th1/Th2 balance in ovalbumin (OVA)-induced asthma model mice, International Immunopharmacology, Apr. 1, 2006, vol. 6, Issue 4, pp. 610-615.
Proposals for GRAS Register Inclusions 2006, retrieved from "http://www.foodsafety.govt.nz/elibrary/industry/grast Proposals_Gras_Register_Inclusions_2006-.htm".
National Institute of Allergy and Infectious Diseases (NIAID) "Guidelines for the Diagnosis and Management of Food Allergy in the United States—Summary of the NIAID—sponsored Expert Panel Report", NIH publication No. 11-7700 Dec. 2010.
Food Allergy from American Academy of Allergy Asthma and Immunology, retrieved from http://www.aaaai.org/conditions-and-treatments/allergies/food-allergies.aspx, Retrieved Oct. 2011.
Ngoc Ly P, Diane R. Gold, Arthur O. Tzianabos, Scott T. Weiss, Juan C. Celedon. "Cytokines, allergy, and asthma," Current Opinion in Allergy and Clinical Immunology 2005; 5: 161-166.
El Biaze M, Boniface S, Koscher V, Mamessier E, Dupuy P, Milhe F et al. "T cell activation, from atopy to asthma: more a paradox than a paradigm," Allergy 2003; 58(9):844-53.
Krug N, Madden J, Redington AE, Lackie P, Djukanovic R, Schauer U et al. "T-cell cytokine profiles evaluated at the single cell level in BAL and blood in allergic asthma," AM J Respir Cell Mol Biol 1996; 14(4):319-26.
Cho SH, Stanciu LA, Begishivili T, Bates PJ, Holgate St, Johnston SL. "Peripheral blood CD4+ and CD8+ T cell type 1 and type 2 cytokine production in atopic asthmatic and normal subjects," Clin Exp Allergy 2002; 32(3):427-33.
Boniface S, Koscher V, Mamessier E, El Biaze M, Dupuy P, Lorec AM et al. "Assessment of T lymphocyte cytokine production in induced sputum from asthmatics: a flow cytometry study," Clin Exp Allergy 2003; 33(9):1238-43.
Cho SH, Stanciu LA, Holgate St, Johnston SL. "Increased interleukin-4, interleukin-5, and interferongamma in airway CD4+ and CD8+ T cells in atopic asthma," Am J Respir Crit Care Med 2005; 171(3):224-30.
Truyen E, Coteur L, Dilissen E, Overbergh L, Dupont LJ, Ceuppens JL et al. "Evaluation of airway inflammation by quantitative Th1/Th2 cytokine mRNA measurement in sputum of asthma patients," Thorax 2006; 61(3):202-8.
Rowe J, Heaton T, Kusel M, Suriyaarachchi D, Serralha M, Holt BJ et al. "High IFN-gamma production by CD+ T celss and early sensitization among infants at high risk of atopy," J Allergy Clin Immunol 2004; 113(4):710-6.
Heaton T, Rowe J, Turner S, Aalberse Rc, de Klerk N, Suriyaarachchi D et al. "An immunoepidemiological approach to asthma: identification of in-vitro T-cell response patterns associated with different wheezing phenotypes in children," Lancet 2005; 365(9454):142-9.
Macaubas C, Sly PD, Burton P, Tiller K, Yabuhara A, Holt BJ et al. "Regulation of T-helper cell responses to inhalant allergen during early childhood," Clin Exp Allergy 1999; 29(9):1223-31.
Smart JM, Kemp AS. "Increased Th1 and Th2 allergen-induced cytokine responses in children with atopic disease," Clin. Exp Allergy 2002; 32(5):796-802.
Corrigan CJ, Kay AB. "CD4 T-lymphocyte activation in acute severe asthma. Relationship to disease severity and status," Am Rev Respir Dis 1990; 141(4 Pt 1):970-7.
Magnan AO, Mely LG, Camilla CA, Badier MM, Montero-Julian FA, Guillot CM et al. "Assessment of the Th1/Th2 paradigm in whole blood in atopy and asthma. Increased IFN-gamma-producing CD8(+) T cells in asthma," Am J Respir Crit Care Med 2000; 161(6):1790-6.
O'Sullivan S, Cormican L, Faul JL, Ichinohe S, Johnston SL, Burke CM et al."Activated, cytotoxic CD8(+) T lymphocytes contribute to the pathology of asthma death," Am J Respir Crit Care Med 2001; 164(4):560-4.
Yazdanbakhsh M, Kremsner PG, van Ree R. "Allergy, parasites, and the hygiene hypothesis," Science 2002; 296: 490-494.
Oosterhout A.J.M. van and Moth A.C. "Th1/Th2 paradigm: not seeing the forest for the trees?" Eur. Respir. J. 2005; 25:591-593.
Casalta Erick C. and Montel Marie-Christine. "Safety assessment of dairy microorganisms: The *Lactococcus* genus," Int. J. Food Microbiol. 2008; 126: 271-273.
Salminen Seppo et al. "Demonstration of safety of probiotics—a review," Int. J. Food. Microbiol. 1998; 44: 93-106.
Kilkkinen et al., "Use of Antimicorbials and risk of type 1 diabetes in a population-based mother-child cohort," Diabetologia (2006) 49: 66-70.
Repa et al., "Mucosal co-application of lactic acid abacteria and allergen induces counter-regulatory immune responses in a murine model of birch pollen allergy," Vaccine vol. 22 (2003) pp. 87-95.
DeBarry et al., "Acinetoacter lwoffii and *lactococcus lactis* strains isolated from farm cowsheds possess strong allergy-protective properties," J. Allergy Clin Immunol. vol. 119, No. 6, (2007) pp. 1514-1521.
Zechini et al., "Endocarditis caused by *Lactococcus lactis* subsp. lactis in a patient with atrial myxoma: a case report," Diagnostic Microbiology and Infectious Disease 56 (2006) 325-328.
Joly-Guillou, "Clinical impact and pathogenicity of Acinetobacter," Clin Microbiol Infect (2005); 11:868-873.
Rathinavelu et al., "Acinetobacter lwoffii invection and gastritis," Microbes and Infection 5 (2003) 651-657.

(56) References Cited

OTHER PUBLICATIONS

Zavros et al., "Gastritis and Hypergastrinemia Due to Acinetobacter lwoffii in Mice," Infection and Immunity, May 2002, p. 2630-2639 vol. 70, No. 5.

Sibbald et al., "Mapping the Pathways to *Staphylococcal* Pathogenesis by Comparative Secretomics," Microbiology and Molecular Biology Reviews, Sep. 2006, p. 755-788 vol. 70, No. 3.

Norton et al., "The immune response to *Lactococcus lactis:* implications for its use as a vaccine delivery vehicle," FEMS Microbiology Letters, vol. 120, Issue 3, pp. 249-256, 1994.

* cited by examiner

Application of arabinogalactan or humic acid

- buffer control
- arabinogalactan 5 μg
- arabinogalactan 1 μg
- humic acid 10 μg
- humic acid 10 μg + arabinogalactan 5 μg
- humic acid 10 μg + arabinogalactan 1 μg

- buffer control
- arabinogalactan 5 μg
- arabinogalactan 1 μg
- humic acid 10 μg
- humic acid 10 μg + arabinogalactan 5 μg
- humic acid 10 μg + arabinogalactan 1 μg

- buffer control
- arabinogalactan gum arabic 5µg
- arabinogalactan Larix 5µg
- arabinogalactan hay 5µg

- buffer control
- arabinogalactan Holcus lanatus 5 µg

COMPOSITION FOR PREVENTION AND TREATMENT OF ALLERGIC AND/OR INFLAMMATORY DISEASES

The present invention refers to an antiallergenic composition comprising at least one arabinogalactan or arabinogalactan protein and/or humic acid.

Overreactions of the body, particularly of the immune system against heterogeneous (foreign) non-injurious compounds are known as allergic reactions or allergic diseases. Said reactions involve the same components of the immune system as an immune reaction against a pathogenic agent.

Several types of allergic immune responses can be distinguished. Allergic reactions of type I involve e.g. bronchial asthma, atopic dermatitis, urticaria, hay fever and food allergy. The number of persons suffering from allergic disorders, chronic inflammatory disorders and/or autoimmune diseases is steadily increasing. The latest statistics show that about 30% of the European citizens suffer from allergies.

Allergic reactions of type I are mediated by IgE antibodies, of which the production is regulated by Th2 cells. Such Th2 cells are present with an increased frequency compared to Th1 cells during allergic diseases. In new born children the Th2 mediated immune response predominates, whereas during the first year of life Th1 mediated response increases and thereafter dominates the immune response (non-allergic response).

Even though the reasons for the occurrence and development of hypersensitivities are not fully understood up to now, it is clear that the development of the immune system is influenced by host and environmental factors. According to the hygiene hypothesis a low frequency of infections and a low microbial exposure during the first years of life may later lead to increased allergic reactions. As the immune response of newborn individuals is based mainly on Th2 cells, while the Th1-dominated immune response needs external stimuli by antigens, it is assumed that in particular the external stimuli by antigens during the early years of an individual's life has a significant influence on the individual's risk of hypersensitivity, in particular in respect to type I allergies.

Possibilities for prevention and therapy of allergic diseases are limited. The symptoms can be alleviated by numerous medications however immunotherapeutical treatment like hyposensitization is still often not successful. Avoiding the contact with allergens as prevention resulted not in decrease of frequency of allergic reactions. Up to now no general preventive measures are established to limit allergic reactions.

The polysaccharide arabinogalactan, particularly arabinogalactan from larch is known to have immune modulating effects. G. S. Kelly describes in *Altern Med Rev*, 1999; 4:96-103 and N. L. Currier et al. in *Phytomedicine*, 2002; 10:145-153 immune enhancing properties of larch arabinogalactan by activation of NK cells. L. S. Kim et al. found in *Altern Med Rev*, 2002; 7:138-149 a stimulation of the components of the immune response in patients after taking larch arabinogalactan, particularly in combination with *Echinacea*.

The structure of arabinogalactan differs dependent from the source for isolation. J. Duan et al. disclose in *Carbohydr Res*, 2003; 338:1291-1297 structural features of arabinogalactan with immunological activity from *Diospyros kaki* and I. Taguchi et al. in *Carbohydr Res*, 2004; 339:763-770 the structure of an immune modulating arabinogalactan from rhizomes of *Atractylodes lancea*. In all the prior literature the effect of arabinogalactan is described as increasing the immediate immune reactions.

L. Brecker et al. describe in *Carbohydr Res*, 2005; 340:657-663 the structural and immunological properties of arabinogalactans from pollen of timothy grass. They discuss the IgE and IgG reactivity of grass pollen allergic and non-allergic individuals.

WO 01/49319 and EP-A 1 637 147 describe a composition or an extract of stable dust for prevention or treatment of allergic diseases.

Use of *Lactococcus* species primarily is described for oral uptake for probiotic approaches (e.g. Kimoto et al., *Microbiol Immunol*, 2004; 4:75-82; Perdigon, G. et al., *Int J Immunopathol Pharmacol*, 1999; 12:97-102; Villamil, L. et al., *Clin Diagn Lab Immunol*, 2002; 9:1318-1323; Vitini E. et al., *Biocell*, 2000; 24:223-32; Perdigon, G. et al. *J Diary Sci*, 1999; 82:1108-14; Huis in't Veld J H., *Ned Tijdschr Tandheelkd*, 1992; 99:467-470), or as carrier for introduction of recombinant genes expressing proteins alleviating any disorder (Cortes-Perez, N. et al., *Clin. Vaccine Immunol*, Published online on 3 Jan. 2007; Daniel, C. et al., *Allergy*, 2006; 61:812-819; DE-A 101 01 793).

*Lactococcus* sp. for prevention and treatment of a disease is disclosed in connection with overweight or diabetes (KR1020010106068), stomach diseases (KR1020040044300) and rheumatic arthritis (EP-A 762 881). An antigen-antitoxin-mixture for preparation of a homeopathic composition for use in the area of heart diseases, hypertension and allergic diseases is described in DE-A 100 07 771.

The object of the present invention was to provide a means or remedy for prevention and/or protection against and/or treatment of allergic and/or inflammatory diseases.

This object is met by a prophylactic antiallergenic composition, comprising at least one arabinogalactan or arabinogalactan protein and/or humic acid.

According to the present invention the term "arabinogalactan" primarily means the arabinogalactan polysaccharide unit which is part of an arabinogalactan protein or arabinogalactan peptide naturally occurring in e.g. various plants. The arabinogalactan can be isolated from said plants by isolating the arabinogalactan protein or peptide and thereafter separating the sugar from the protein/peptide or by using an isolation technique where the arabinogalactan immediately is separated and can be isolated as such. For the purposes of the present invention the isolated arabinogalactan is preferred, however, the effect of the arabinogalactan is not significantly decreased when the arabinogalactan protein or peptide is used. Therefore it is not relevant to separate the arabinogalactan from the protein/peptide, as long as the arabinogalactan is present in the composition according to the invention.

In a preferred embodiment the composition contains at least one arabinogalactan. Arabinogalactans of different plants may have different structures, particularly concerning the sugar composition, sequence and bonding type. Thus, different 3D structures of the arabinogalactans result depending on the preparation pathways of the plant which is the source for isolation.

According to the invention any arabinogalactan can be used, however, preferably the arabinogalactan is one isolatable from any grass. With "isolatable" is meant that the arabinogalactan is either isolated from a natural source, which is preferably a grass, or the arabinogalactan is isolated from any other source or is artificially prepared (e.g. synthesized), however has the same structure as an arabinogalactan isolated from the natural source (preferably grass). One preferred arabinogalactan is isolatable from Meadow Foxtail (*Alopecurus pratensis*), another preferred one can be isolated from timothy grass and timothy grass pollen (*Phleum pratense* L)

or Cock's Foot (*Dactylis glomerata*) or Yorkshire Fog (*Holcus lannatus*) or English Raygrass (*Lolium perenne*) or Smooth Meadow grass (*Poa pratense*) or Rye (*Secale cereale*) or grasses from related species as well as mixtures of at least two of these preferred arabinogalactans can be used.

Figure 1B:
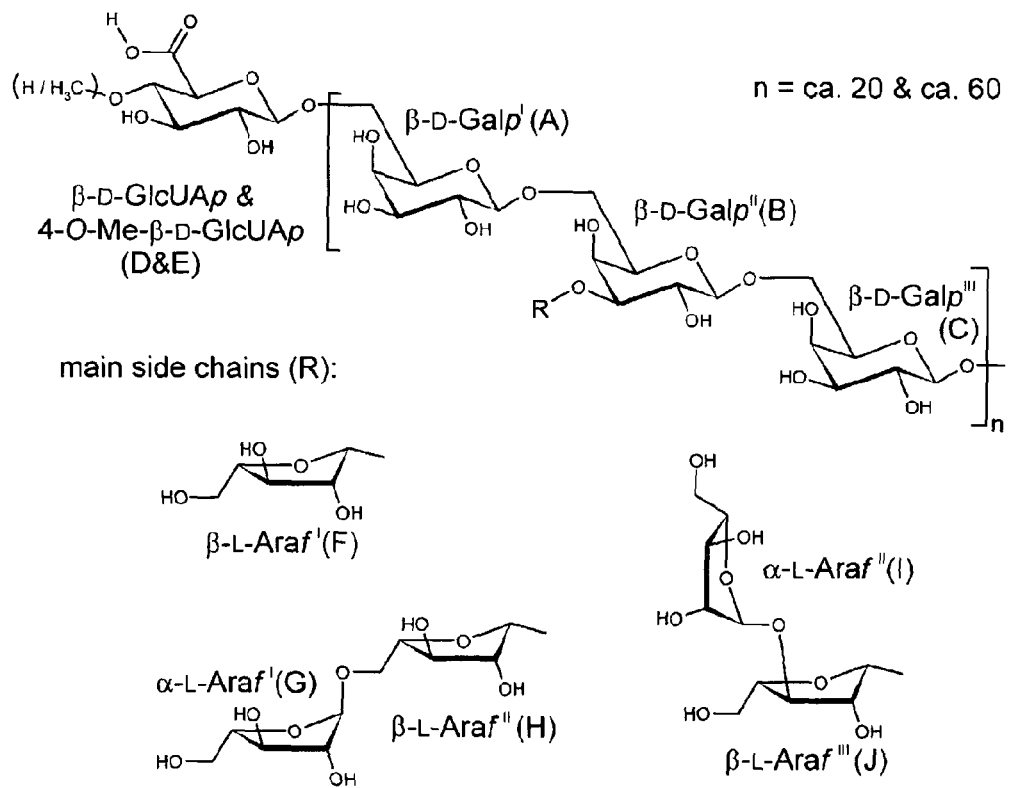
Figure 2:
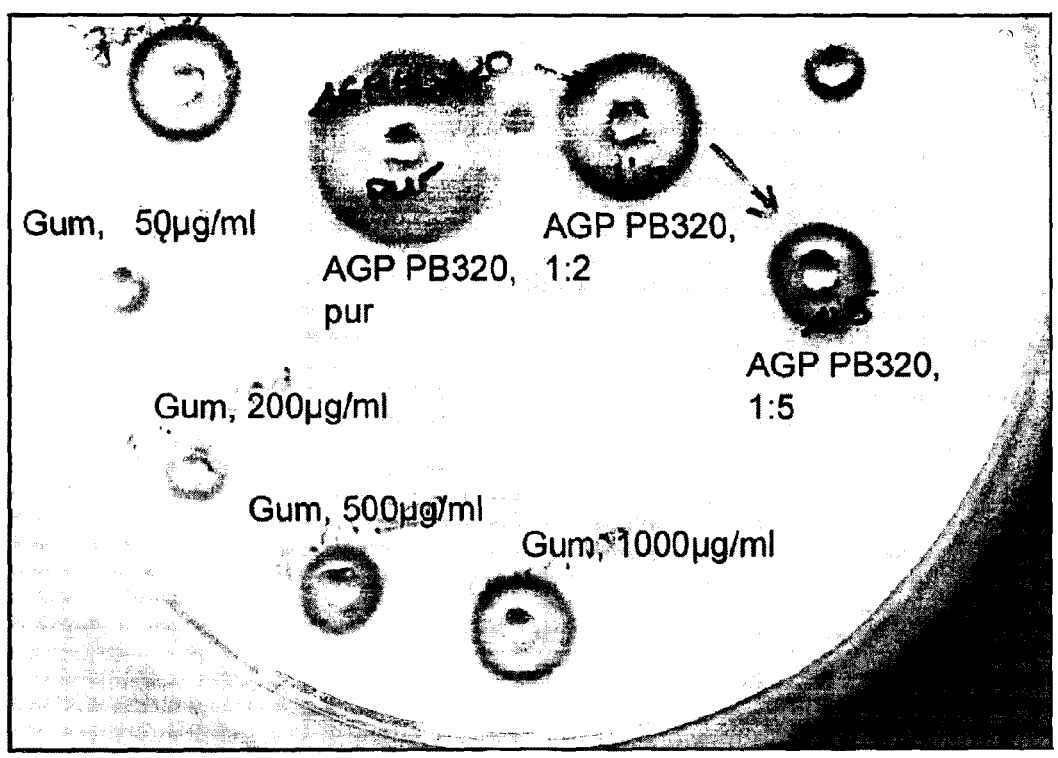

Particularly preferred is an arabinogalactan having a structure shown in FIG. 1a and FIG. 1b. An arabinogalactan having a structure as shown in FIG. 1a and FIG. 1b according to the present invention can be used as a means or remedy or medicament as such without any further active ingredient for the prevention, protection against or treatment of any of the diseases mentioned below, since such an arabinogalactan has a particularly high effect already alone. As well a mixture of at least one of the preferred arabinogalactans with at least one further arabinogalactan can be used without any further active ingredient.

Figure 3:
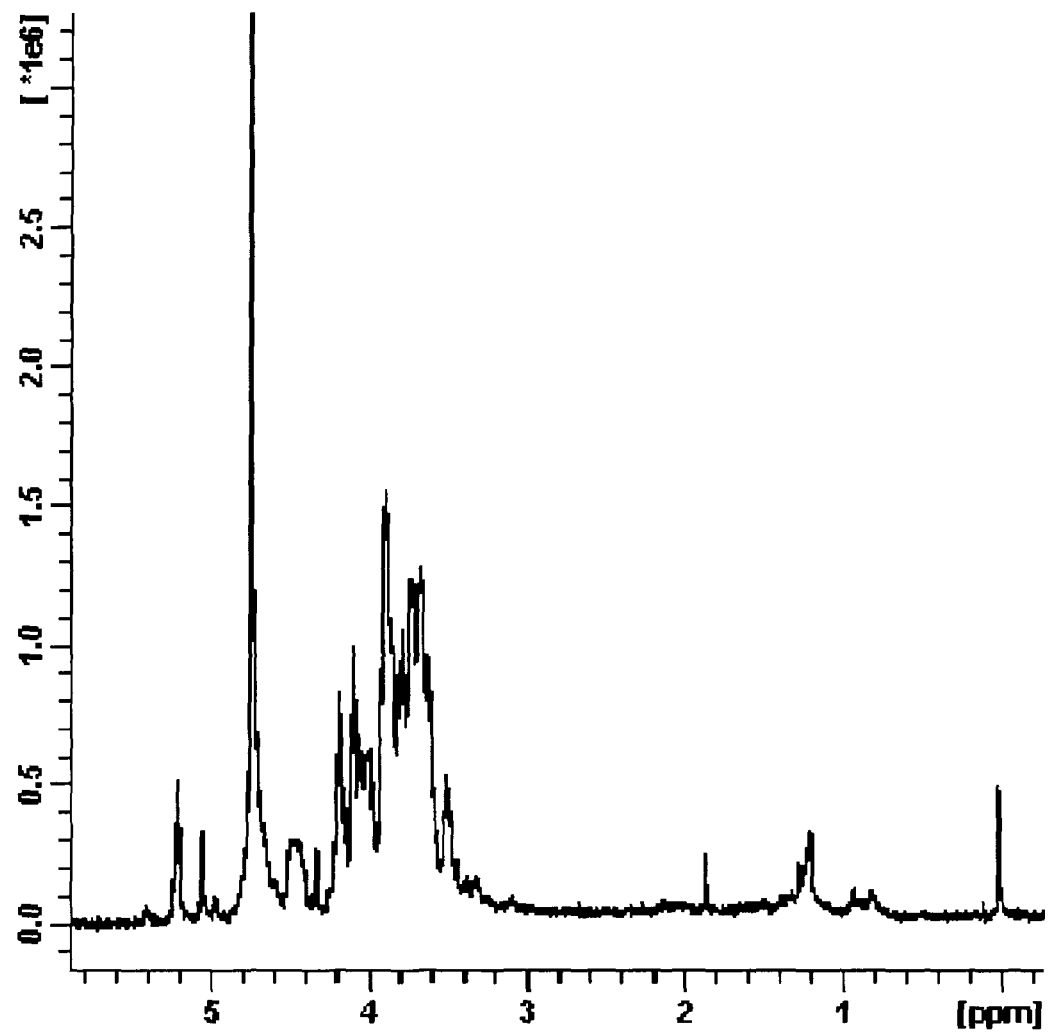

Humic acid is one product of decomposition of organic material and has a structure shown in FIG. 3. Humic acid has an immunomodulating effect in living organisms as it is shown in the examples below and therefore can be used alone for prevention, protection or treatment of the diseases discussed herein. However, preferably according to the invention humic acid is used in combination with at least one arabinogalactan, particularly preferred with at least one of the arabinogalactans which are mentioned above as preferred.

Thus, in a preferred embodiment the composition of the present invention comprises (a) at least one arabinogalactan or arabinogalactan protein and at least one further active ingredient selected from the group of (b) naturally occurring, isolated bacteria of the genus *Lactococcus* or fragments thereof and/or (c) humic acid.

The term "naturally occurring" bacteria means, that the bacterium/bacteria is/are not genetically engineered and is/are isolatable from any natural source. With "isolatable" as well is meant that the bacteria can be isolated from a natural source, however, as well they can be grown and cultivated under defined conditions, e.g. as cell cultures.

The present invention involves the use of bacteria of the genus *Lactococcus* as naturally occurring, non-genetically engineered, particularly non-transgenic microbe. Preferably said bacteria are used in isolated form. This means that either at least one *Lactococcus* species, preferably *L. lactis*, or a mixture of *Lactococcus* species in isolated and optionally purified form are added to the pharmaceutical composition. Further fragments of the bacteria can be used. The term "fragments" is used here for membrane parts and membrane ingredients, cell wall proteins, particularly glycosylated proteins (others than arabinogalactan proteins), polysaccharides (others than arabinogalactan), lipopolysaccharides (endotoxines), cytosolic proteins, molecules and/or compounds and/or metabolites expressed or synthesized by the bacteria, nucleic acids and/or any other ingredient which is part of the original bacterium. As well a mixture of bacteria fragments and undestroyed bacteria can be used.

The non-fragmented bacteria can be used as living organisms or after any denaturation step. Since the mentioned bacteria themselves are harmless for mammal organisms the use in vital form corresponds to natural occurrence and is a preferred embodiment of the invention. To avoid contamination of the composition with other microorganisms less harmless than Lactococci, according to the invention a method for sterilisation of the composition can be applied like e.g. using an autoclave, cooking or heating the organisms, use of bactericides, bacteriastatica, fungicides, fungistatica, viricides and/or viristatica, UV rays or use of organic solutions which are toxic for bacteria like e.g. alcohols, particularly ethanol, propanol, isopropanol etc., lyophilisation or sterilisation by coldness.

The combination of (a) at least one arabinogalactan or arabinogalactan protein with at least one of the components (b) and (c) increases the effect of the application of arabinogalactan alone. Whereas (a) induces a significant proinflammatory response and a tolerization of the immunological T-cell response by downregulating both Th1 and Th2 activation as demonstrated by suppression of cytokines in stimulated spleen cells from mice and downregulation of all antibody responses, (b) also activates proinflammatory cytokines and selectively activates Th1 response. Instead, (c) does not activate proinflammation but at the same time leads to a tolerance effect.

One advantage of the composition of the present application is that all the ingredients themselves are absolutely harmless for mammals, however, according to the present invention it has been found that they can be used for long term prevention or protection against allergic or inflammatory diseases. Arabinogalactan, the mentioned bacteria as well as humic acid can be found anywhere in the environment and no negative influence for good health is known. Application of at least arabinogalactan, preferably the composition of the present invention before any onset of an allergic or an inflammatory disease can prevent such a disease or can alleviate the violence of outbreak. This is what is meant with "prevention" or "protection".

The origin of the ingredients (a), (b) and/or (c) is not relevant for the present invention as long as they fulfil the requirements that they are harmless, and they correspond to the definition given above for the ingredients (a), (b) and (c). Sources for isolation of the arabinogalactan preferably is grass and for the bacteria preferably are grass, hay, dust of houses, dust of cowsheds, food, fruits and similar. After isolation the ingredients may be purified or cultivated (bacteria). However, as well the ingredients can be commercially obtained.

For preparation of a composition according to the present invention each of the components (a), (b) and/or (c) can be isolated from any suitable source and optionally purified or can be commercially obtained. Preferably at least one of the preferred arabinogalactans, e.g. as shown in FIG. 1a and FIG. 1b, are either mixed with component (b) or with component (c) or with both and/or optionally with a suitable carrier. The carrier either can be a dissolvent like e.g. water or an alcohol, without being limited to these, or a solution as mentioned above, or can be any suitable dry carrier like e.g. ground silicate, starch, cellulose and cellulose derivatives and similar without being limited to these.

The order of addition of each of the components (a), (b) and/or (c) to result in the composition is not relevant and depends only on their availability and the comfort of the preparing person or device. For example a liquid composition containing at least component (a) and optionally at least one of the components (b) and (c) are prepared by addition of at least one arabinogalactan to an aqueous or aqueous-alcoholic solution, thereafter optionally either adding one of the components (b) and (c) or adding both sequentially or both together.

Addition of the bacteria (b) may be employed either directly after isolation and optional purification or they can be denaturated and/or fragmented before they are added to the other ingredients or the carrier. Furthermore any sterilisation step can be carried out or any sterilizing agent can be added to the composition, e.g. any of the sterilizing methods or agents mentioned above.

Humic acid as component (c) as well can be added directly after isolation or as a commercially available product.

Either each of the components or the ready-prepared composition can be lyophilized after preparation to provide a storage stable product for direct application or for uptake with water or any other suitable solvent before use.

Diseases which can be prevented or treated by this harmless and careful application are particularly allergic and chronic inflammatory diseases, like IgE-depending Type I allergic diseases or Type IV allergic diseases and chronic inflammatory diseases or autoimmune diseases. Examples therefore are hay fever, food allergy, asthma, urticaria, neurodermitis, atopic dermatitis, contact eczema, psoriasis, diabetes type 1 or 2, multiple sclerosis, rheumatoid arthritis, diseases of the thyroid gland like Hashimoto Thyreoditis and Graves disease.

According to the present invention at least one arabinogalactan or the composition can be applied already immediately after birth of a child or during the first life period. The composition is suitable for application for infants (babies) or pregnant women, e.g. for whom is known due to a positive family anamnesis that they have an increased risk to develop any allergic or chronic inflammatory disease or which show first signs of such disease. Prevention for the infants may already be obtained by application of the arabinogalactan or the composition according to the invention to the pregnant mother.

The composition is suitable and can serve for modification of the infant and adult immune system. Therefore the composition or the ingredients (a), (b) and/or (c) can be applied to pregnant women, infants (babies), children during the first years of life (up to 8-10 years) and adults for treatment preferably repetitively. Preferably the composition or the ingredients are applied to pregnant women, infants, children or adults who have due to several diagnostic features an increased risk to develop any allergic or chronic inflammatory disease. The composition or the ingredients (a), (b) and/or (c) can also be applied to pregnant women, infants, children or adults who already show first signs of an allergic or chronic inflammatory disease. An increased risk as well can be determined by genetic analysis.

One advantage of the present invention is high efficacy whereas the inventive composition can be applied by any easy conventional route. Application can be via oral, nasal, conjunctival, inhalative, subcutaneous, intra-articular, intraperitoneal, rectal or vaginal route. Oral, nasal or inhalative application is preferred.

Thus in a preferred embodiment of the present invention the composition is provided as a pharmaceutical composition in form of an aerosol, solution, preferably aqueous or aqueous-alcoholic solution, suspension, lyophilisate, powder, tablet or suppository. Most of these embodiments are particularly suitable for nasal, oral or inhalative application.

An aerosol according to the invention comprises small solid or liquid particles, which can be prepared by an inhalator, a fogging device or respiratory device. The particles of the aerosol can consist of the composition or can contain the composition in combination with a suitable supporting material. The aerosol can have a particle size e.g. of up to 100 μm for nasal application. For inhalative use the aerosol preferably has a particle size of up to 10 μm, preferred of up to 5 μm.

A solution according to the invention can contain at least one arabinogalactan and optionally at least one of components (b), preferably soluble fragments of components (b), and/or component (c) preferably in form of an aqueous solution or an aqueous-alcoholic solution. Examples are a mixture of water with components (a), (b) and/or (c) or of aqueous solutions with ethanol, propanol or isopropanol. Said solution can be buffered or can contain further optional ingredients like salt, preferably salt in isotonic amounts (e.g. physiological isotonic NaCl solution). Further said solution can contain further harmless ingredients, e.g. natural or synthetic additives like conserving agents, stabilizers, flavours like sugar, pharmaceutically suitable carriers, emulsifiers, diluents and if desired natural dying agents.

In case that the bacteria as component (b) are used in form of living organisms, undestroyed but denaturated organisms or insoluble fragments thereof the composition can be in form of a suspension. For suspension of component (b) in this form a solution can be used as described above.

Further, the composition can be a lyophilisate or a powder or can be mixed with a pharmaceutically applicable powder. Such a lyophilisate or powder can be combined with any further pharmaceutically acceptable ingredients, e.g. for application with a powder inhalator. Furthermore the powder or lyophilisate can be used to prepare a tablet or suppository for oral, anal or vaginal application.

Preferably for prevention the composition or the active ingredients are applied to pregnant women, infants or children within the first five years of life, more preferably within the first two years of life or to adults with a risk of respective diseases. The composition may be applied by any commonly known route, preferably by an inhalator, evaporator, fogging device, atomizer or respiratory device. It can be applied periodically over a longer time period to obtain a continued stimulation in the organism. E.g. the composition or the active ingredients can be applied up to 10 years once up to 21 times per week, preferably 7 times to 14 times per week. Application can be obtained by injection of a spray in the nose or by inhalation. In the last case the duration can be between 1 and 120 minutes, preferably between 5 and 60 minutes.

Application of the prepared composition can be carried out by any suitable means.

For prevention the components (a), (b), and (c) alone or in combination are applied in a concentration of 1 ng to 100 g/day or $10^2$ to $10^{11}$ cfu/day, respectively. Preferably the components (a), (b), and (c) are applied in a concentration of 1 μg to 10 g/day or $10^4$ to $10^{10}$ cfu/day, respectively.

In addition to the pharmaceutical compositions described above the present invention further provides a prophylactic antiallergenic, i.e. health-improving indoor air product. In this embodiment the composition described above is provided in a form suitable to be distributed in the indoor air and forms part of an indoor air product.

In particular for infants (babies), conventional pharmaceutical application routes often are problematic. Whilst subcutaneous, intra-articular and intra-peritoneal administration routes are unpleasant or even painful for the patient and often require the application by trained staff, even non-invasive administration routes such as oral, nasal, rectal or inhalative routes are difficult to handle in the treatment of very young patients, in particular babies, as the patient has to put on a facemask or insert a mouthpiece into his mouth and to stay calm during the time the composition is administered. In particular, if the composition shall be applied (periodically or not) over a longer time period to obtain a continuous stimulation in the organism, these inhalative procedures may be annoying.

Figure 4:
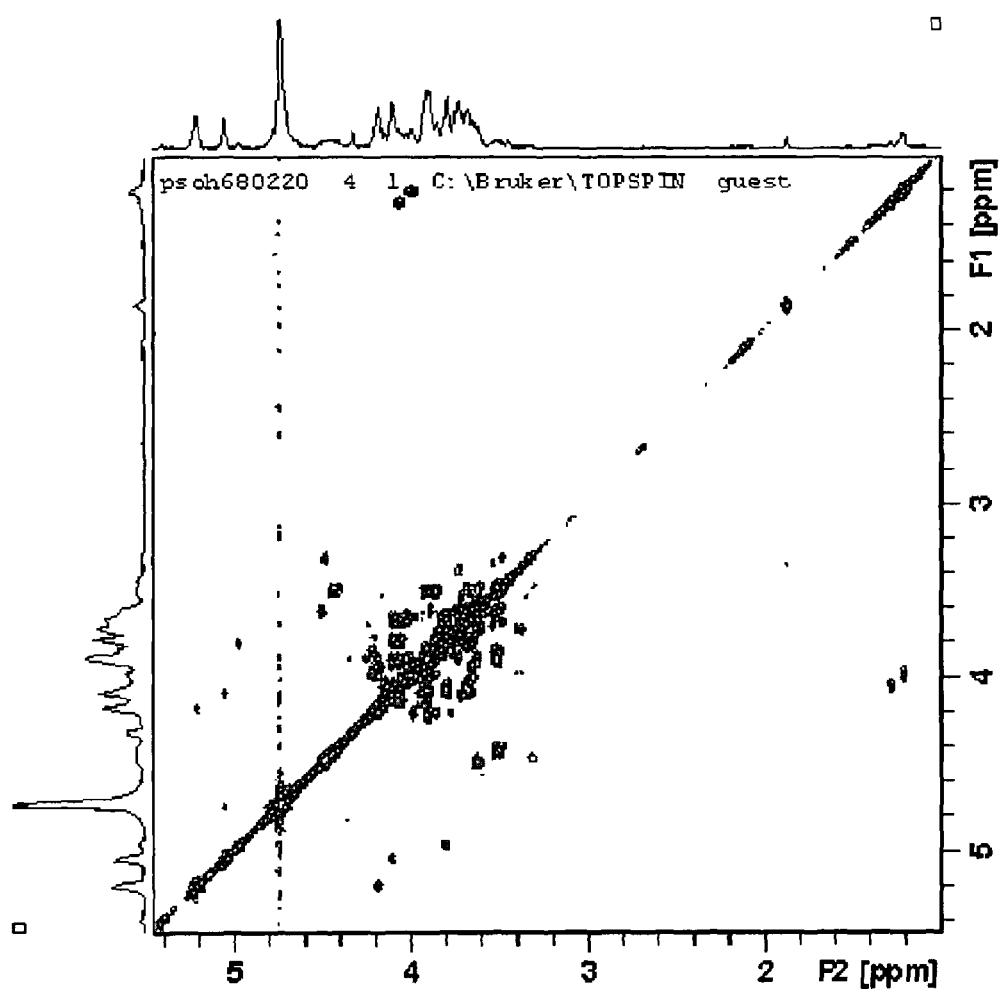
Figure 5:
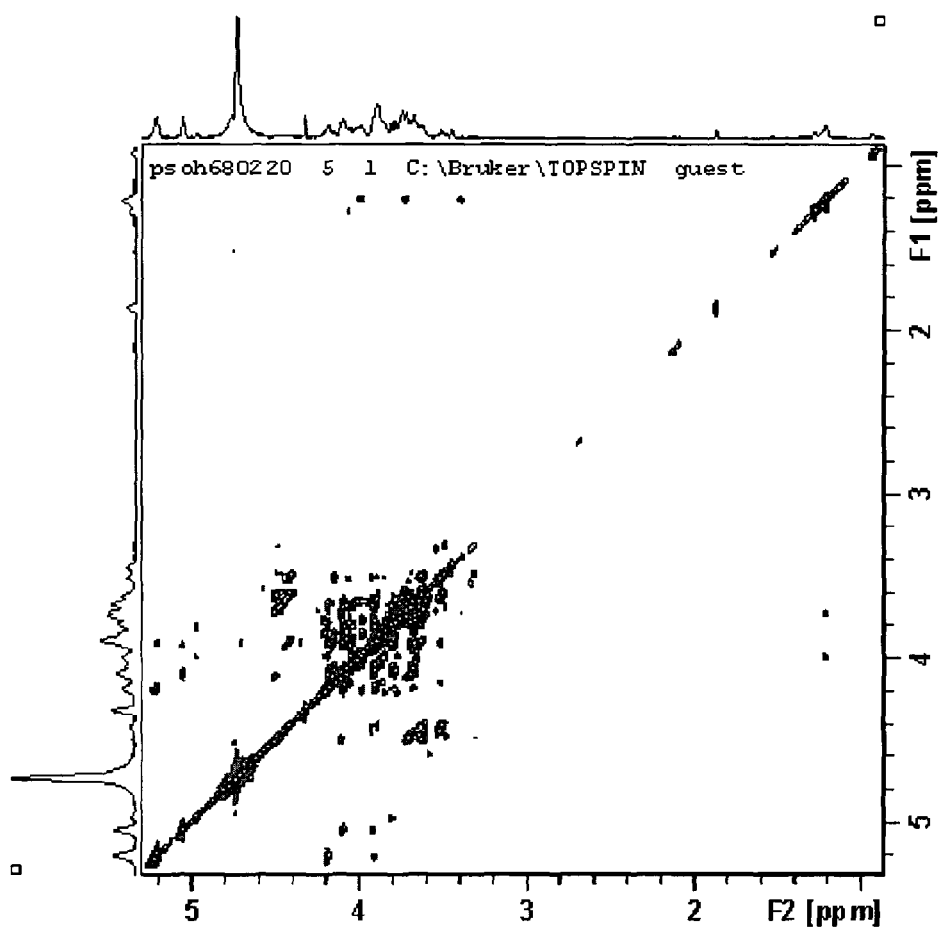
Figure 6:
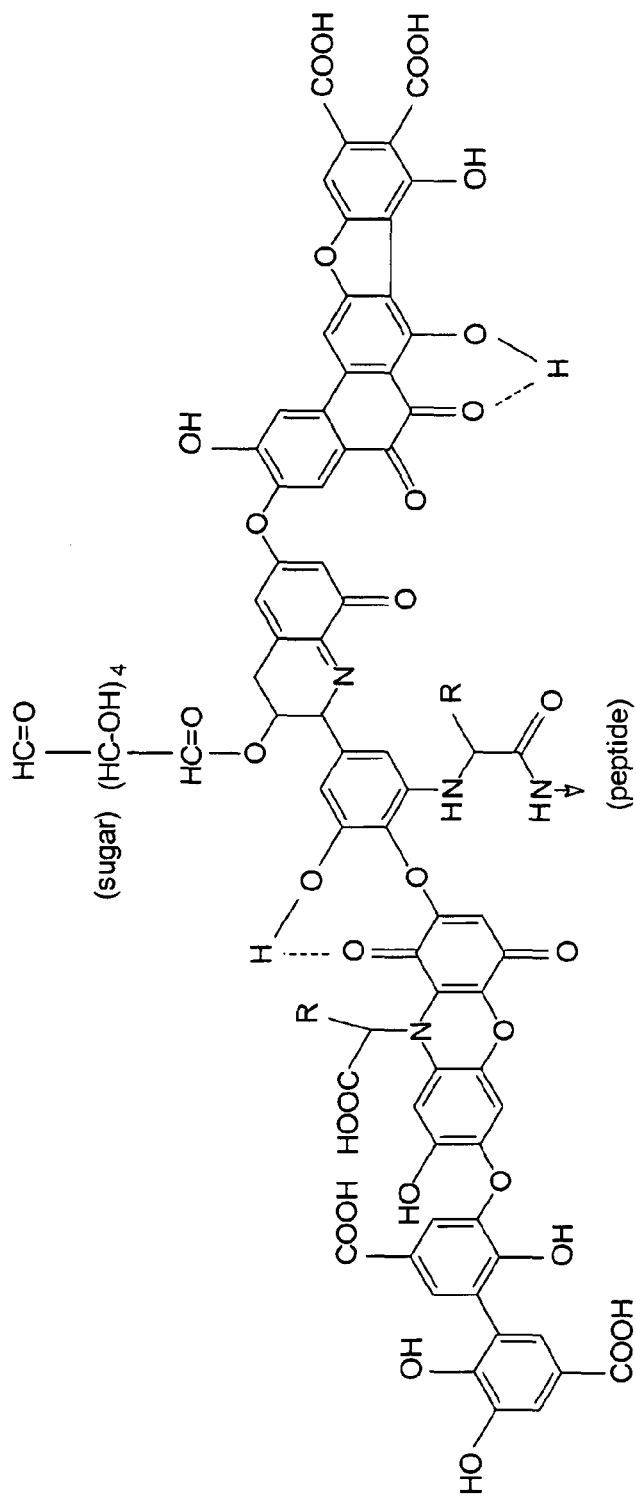

Accordingly, the present invention further provides a composition comprising at least one arabinogalactan or arabinogalactan protein and/or humic acid, as described above, for the prophylaxis and/or treatment of allergic or chronic inflammatory diseases, that does not have to be administered via conventional pharmaceutical routes, i.e. oral, subcutaneous, intra-articular, intra-peritoneal, rectal, vaginal, conjunctival, nasal or inhalative routes using an inhaler, nebulizer or vaporizer equipped with a mouthpiece/facemask. Instead, the indoor product of the present invention comprises the composition of the present invention in a form suitable to be distributed in the indoor air.

Instead of administering a pharmaceutical composition to one single individual, the composition forming part of the indoor air product can be simply distributed in the indoor air to generate a health-improving indoor air, thus simulating the healthy air in natural farming environments.

The indoor air product of the present invention has several advantages over conventional pharmaceutical compositions. First of all, since it is neither directly introduced into the patient's body nor administered via an apparatus which is in direct contact to the patient's body, the composition comprised therein may be easily administered to very young children, and even newborn babies. By distributing the composition in the indoor air, all persons present in the room participate on the health-improving effect. It is furthermore possible to create a continuous concentration of the active ingredients in the indoor air, thus avoiding the exposure of a patient to one huge single dose, guaranteeing a continuous stimulation of the immune system and a gentle and mild uptake even in very small children.

Instead of distributing the composition in the indoor air, the composition may also be sprayed on items the child often comes into contact with, such as soft toys, upholstery, bed linen, mattresses, pillows, blankets, and the like.

In terms of the present invention "indoor air" is the (breathing) air inside a closed or closable space usually occupied by human beings, for example a residence, an office or a public building or a vehicle, a plane, a train and the like.

The composition may be prepared as explained above, i.e. any of the aforementioned functional ingredients may be obtained by harvesting from natural sources, chemical synthesis, or biotechnological procedures and mixing them afterwards. If the composition comprises more than one functional ingredient, each of said ingredients may be independently harvested from a natural source, chemically synthesized, or biotechnologically produced. If two or more functional ingredients present in one composition are obtained in the same way, i.e. both harvested from natural sources, they may be obtained in the same procedure, i.e. simultaneously harvested from the same origin, or may be harvested from different origins and thereafter mixed together.

The arabinogalactan may be used in an isolated from, i.e. separated from any further organic (plant or bacterial) material of its natural origin, but in particular in the indoor air product of the present invention it may as well be used in a form in which it is bound or otherwise associated to organic material of its natural origin.

In a preferred embodiment of the indoor air product of the present invention, however, the composition comprises the functional ingredients, i.e. the arabinogalactan, arabinogalactan protein and/or humic acid and further active ingredients, in the form of a stable dust extract, a hay extract, or a grass extract, or a mixture thereof. These extracts usually comprise more than one functional ingredient in the sense of the present invention. Thus, the use of an extract offers the possibility for simultaneously obtaining more than one functional ingredient in one single process step. To these extracts naturally occurring, non-pathologic, non-transgenic isolated bacteria, said bacteria preferably being selected from the group consisting of *Lactococcus* and *Acinetobacter*, or fragments thereof, or mixtures thereof may be added.

Methods for collecting stable dust are known in the state of the art and are described for example in M. Peters et al., *Thorax* 2006, 61:134-139; EP 1 637 147 A1 and WO 01/49319. For example sediments from cattle and goat stables can be collected by scraping off all surfaces inside the stables at height of 0.5 to 1.5 meters (rags, tables, tools) with a metal spatula. Preferably only dry dust is collected, and the collection of moist or wet dust preferably is avoided. The collected dust is then passed through a conventional kitchen sieve. Afterwards, dust samples from different origins may be combined.

Extracts from stable dust samples may be obtained by any method known to a person skilled in the art for this purpose. It is, however, preferred to use the following procedure: At first the dust samples are optionally homogenized, for example using a mortar, a triturator or a mill. The dust is then suspended in water or isotonic saline (0.9% aqueous solution of sodium chloride) at room temperature (20 to 25° C.), preferably 22° C., after which a certain amount of glass beads, preferably having a diameter of 0.1 to 2 mm, more preferably 0.4 to 0.6 mm, are added and the mixture is mechanically disintegrated, for example by using a homogenizer or a shaking apparatus for several hours. After disintegration is judged completed, the sample components are separated by centrifugation, the supernatant is collected, dialyzed against water and then lyophilized.

Stable dust samples may also be collected using an impactor, as described for example in WO 01/49319. Microorganisms, in particular bacteria, may be obtained from such samples using cell culture. Specific strains may be collected from such cultivated samples, isolated and further cultivated, as described for example in EP 1 964 570 A1.

As explained above, the extraction solvent preferably is water, more preferably isotonic saline. After obtaining the extract using the extracting agent, the solution obtained may be lyophilized in order to obtain a dry powdered substance, or the extract may be directly processed further.

In the composition of the health-improving indoor air product of the present invention the one or more functional ingredients preferably are dispersed or dissolved in a solvent, preferably in water, more preferably in isotonic saline. The composition comprised in the indoor air product of the present invention may additionally comprise a finely divided excipient, preferably a solid excipient, more preferably selected from the group consisting of lactose, sodium chloride, acetate, citrate, lactate, sulfite or benzoate. Said excipient acts as an inert carrier substance, improving the suspension stability, dosing precision, and chemical stability of the functional ingredient. The composition comprised in the indoor air product of the present invention additionally may comprise a propellant, preferably selected from the group consisting ofbutane, propane, carbon dioxide or compressed air. The propellant preferably is free from any fluorochlorinated hydrocarbons (CFC).

In order to improve homogeneity of the composition, said composition additionally may comprise a surface-active agent or emulsifier. Any suitable agent can be used without any restriction of the invention, however, preferably the surface-active agent or emulsifier is selected from the group consisting of commonly known phosphates, polysorbates, lecithine, mono- or diglycerides or other fatty acid derivatives.

The amount of functional ingredients in the composition preferably is in the range of 0.001 to 20 mg/ml, more preferred 0.01 to 15 mg/ml and even more preferred 0.1 to 10 mg/ml.

The indoor air product composition of the present invention preferably additionally comprises (1) a container for storing the composition and (2) a dispenser for distributing the composition in the indoor air, wherein the composition preferably is distributed in the indoor air in the form of a plurality of spray droplets or finely divided particles. Said spray droplets or particles preferably have a diameter in the range of from 1 to 500 μm, preferably 5 to 300 μm The size and shape of the container are not particularly limited. Any container for storing a room spray composition known in the state of the art may be used. The propellant and at least one functional ingredient may be comprised in the same storage container or may be comprised in separate containers, and mixed only upon the process of distributing the composition in the indoor air. Preferably, the container is equipped with a fixing device for fixation at the wall, room ceiling or rod of a bed or other furniture. Depending upon the type of dispenser used, the shape of the container is adapted to the type and shape of dispenser, which is well-known to a person skilled in the art.

The dispenser preferably is selected from the group consisting of foggers, nebulizers, or sprayers. Any type of dispenser suitable for distributing/spraying liquids is usable according to the present invention and doesn't restrict the inventive concept. For example a refillable and reusable container and dispenser is a preferred embodiment wherein the liquid composition comprising the functional ingredient(s) can be refilled in the container. Further for example the inventive composition can be distributed in the indoor air by an air humidifier.

The composition comprised in the indoor air product of the present invention can be used for generating a health-improving indoor air.

Accordingly, the present invention also comprises a method of generating a health-improving indoor air, comprising the step of distributing the composition of the indoor air product of the present invention in form of a plurality of spray droplets or particles in the indoor air.

In the inventive method, the composition is preferably distributed in the indoor air by using a dispenser as described above.

FIGURES

FIG. 1*a* and FIG. 1*b*: Structure of arabinogalactan isolatable from timothy grass pollen (*Phleum pratense* L.). According to NMR spectroscopical analyses (see FIG. 2-4 and Table 1), the arabinogalactan from Meadow foxtail (*Alopecurus pratensis*) comprises very similar structures.

FIG. 1 *a*: Structural detail of arabinogalacan 1 of *Phleum pratense*. L. Brecker et al. Carbohydr Res, 2005; 340:657-663

FIG. 1 *b*: Structural detail of arabinogalacan 2 of *Phleum pratense*. L. Brecker et al. *Carbohydr Res,* 2005; 340:657-663

FIG. 2: Concentration of arabinogalactan isolated from *A. pratensis* (AGP PB320) compared to known concentrations of arabinogalactan from gum Arabic by means of radial diffusion assay.

FIG. 3: 1D $^1$H NMR spectrum of the arabinogalactan from *Alopecurus pratensis.*

FIG. 4: 2D $^1$H, $^1$H correlation spectrum (COSY) of the arabinogalactan from *Alopecurus pratensis.*

FIG. 5: 2D $^1$H, $^1$H total correlation spectrum (TOCSY) of the arabinogalactan from *Alopecurus pratensis.*

FIG. 6: Structure of humic acid

FIG. 7: Sensitization and treatment protocol for eliciting asthma in mice and treatment with arabinogalactan or humic acid. See example 2.1

FIG. 8: Number of eosinophilic granulocytes in airways of mice that were sensitized with ovalbumin and treated with either arabinogalactan or humic acid. See Example 2.2.

FIG. 9: Infiltration of eosinophilic granulozytes in mice that were treated with *Lactococcus lactis* during sensitization. See Example 2.2.

FIG. 10: Interleukin-5 production of splenocytes of mice that were treated with arabinogalactan or humic acid. See Example 2.2.

FIG. 11: Measurement of local IgE production in mice that were treated with arabinogalactan or humic acid during sensitization. See Example 2.3.

FIG. 12: Number of eosinophilic granulocytes in airways of mice that were sensitized with ovalbumin and treated with combinations of *Lactococcus lactis* and arabinogalactan during sensitization. See Example 2.4.

FIG. 13: Measurement of local IgE production in mice that were sensitized with ovalbumin and treated with combinations of *Lactococcus lactis* and arabinogalactan during sensitization. See Example 2.4.

FIG. 14: Number of eosinophilic granulocytes in airways of mice that were sensitized with ovalbumin and treated with combinations of arabinogalactan and humic acid during sensitization. See Example 2.5.

FIG. 15: Measurement of local IgE production in mice that were treated with combinations of *Lactococcus lactis* and arabinogalactan during sensitization. See Example 2.5.

FIG. 16: Number of eosinophilic granulocytes in airways of mice that were sensitized with ovalbumin and treated with arabinogalactan from gum arabic, larch (*Larix*) or hay during sensitization. See Example 2.6.

FIG. 17: Number of eosinophilic granulocytes in airways of mice that were sensitized with ovalbumin and treated with arabinogalactan from Yorkshire Fog (*Holcus lanatus*) during sensitization. See Example 2.7.

EXAMPLES

Example 1

Isolation of Arabinogalactan

Freshly collected *A. pratensis* plants were frozen in liquid nitrogen and grinded in a mortar. Pulverized material was extracted with isotonic sodium chloride solution and subsequently dialyzed against water. All extracts were stored lyophilized. After resolubilization at 100 mg/ml in isotonic aqueous NaCl solution extracts were sterile filtered (0.22 μm) before usage. 1 Mililiter was applied to a Superdex 200 prep grade gel filtration column and eluted with 0.9% aqueous NaCl solution. Fractions with 1 ml volume were collected and sugar was detected in the collected fractions colometrically by means of resorcin reaction. For precipitation 1 mg from the high molecular mass fraction was mixed with 1 mg β-glycosyl Yariv reagent. The resulting precipitate was washed two times with 0.9% aqueous NaCl solution and dissolved in 10% (w/v) sodium dithionite ($Na_2S_2O_4$) by heating to 50° C. until the color changed from red to light yellow. Finally the solution was dialysed extensively against water. AG concentration was measured by radial diffusion with gum Arabic AGP as standard. The example shows a sample with a concentration of 4 mg/ml (FIG. 2).

Isolated arabinogalactan from *A. pratensis* was investigated by NMR, COSY and TOCSY analysis. Results are shown in FIGS. 3, 4 and 5. The structure of said arabinogalactan appears very similar to the arabinogalactan from *Phleum pratense* shown in FIG. 1a and FIG. 1b

TABLE 1

Proton (ppm) chemical shifts of the arabinogalactan from *Alopecurus pratensis*. The numbering of the Araf and Galp residues is according to L. Brecker et al. *Carbohydr Res*, 2005; 340: 657-663.

| Residue | H-1 | H-2 | H-3 | H-4 | H-5(a) | H-5b | H-6a | H-6b |
|---|---|---|---|---|---|---|---|---|
| β-Araf I | 5.21 | 4.19 | 3.91 | 4.10 | 3.80 | 3.68 | — | — |
| α-Araf I | 5.06 | 4.10 | 3.94 | n.d. | 3.81 | 3.70 | — | — |
| α-Araf II | 4.98 | 3.81 | 4.00 | n.d. | n.d. | n.d. | — | — |
| β-Galp I | 4.40 | 3.51 | 3.63 | 3.90 | n.d. | — | n.d. | n.d. |
| β-Galp II | 4.49 | 3.62 | 3.70 | 4.11 | n.d. | — | n.d. | n.d. |
| β-Galp III | 4.42 | 3.51 | 3.63 | 3.95 | n.d. | — | n.d. | n.d. | n.d., not detected.

Example 2

Effectiveness of Arabinogalactan In Vivo 2.1. Sensibilization and Induction of Allergic Asthma in Mice by Ovalbumin (OVA)

Mice were sensitized by intraperitoneal injection of 20 μg ovalbumin (OVA; GradeV; Sigma, St. Louis, Mo.) emulsified in 2.2 mg aluminum hydroxide (Imject Alum; Pierce, Rockford, Ill.) in a total volume of 200 μl on days 1 and 14. On days 28 and 38 mice were challenged via the airways with 1% OVA aerosol for 20 min (FIG. 7) using a PARI-Boy aerosol generator. Controls were injected with aluminum hydroxide alone and challenged with PBS aerosol (non-sensitized).

Figure 7:
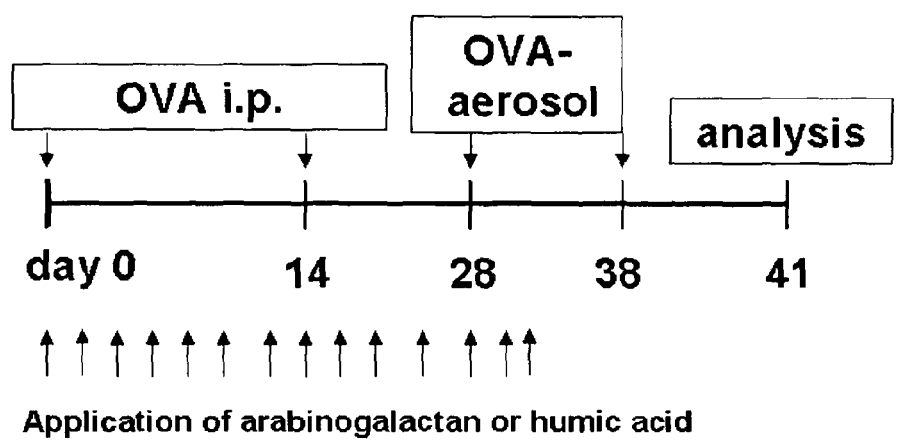

Treatment of mice was done by intranasal application of arabinogalactan (0.5 μg or 5 μg) or humic acid (1 μg or 10 μg) in 50 μl volume or by intranasal application of $10^8$ cfu lyophilized bacteria, respectively. Mice were treated for a total of 14 times starting on day 1 of sensitization with the last application 10 days before the final challenge. For this procedure mice were anesthetized with a mixture of Ketamin and Xylazin. The sensitization and treatment protocol is shown in FIG. 7.

2.2. Examination of Cellular Composition of Broncho-Alveolar Lavage (BAL)

After treatment of mice with arabinogalactan, humic acid or *Lactococcus lactis* during sensitization eosinophilic infiltration of cells in the airways were analyzed. Since eosinophilia depends on IL-5 production of Th2 cells production of this cytokine after restimulation of cells with allergen was also studied.

Figure 8:
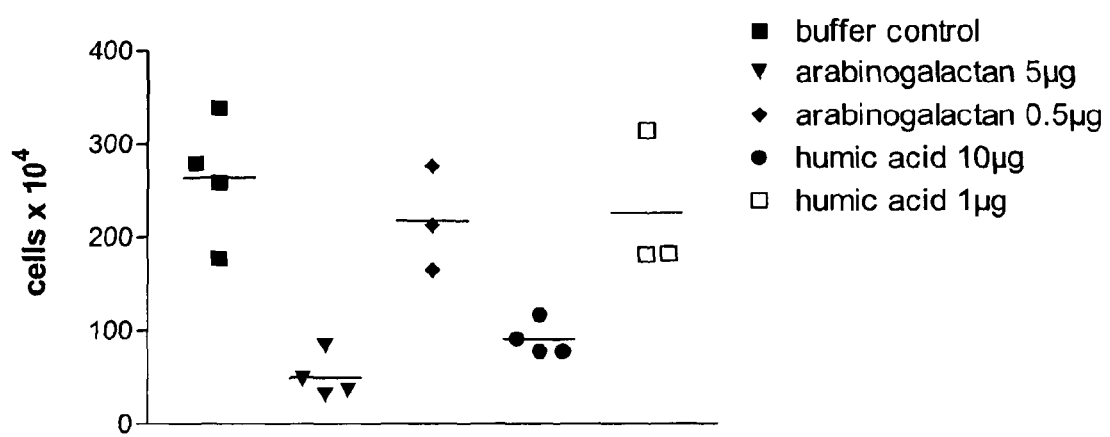
Figure 9:
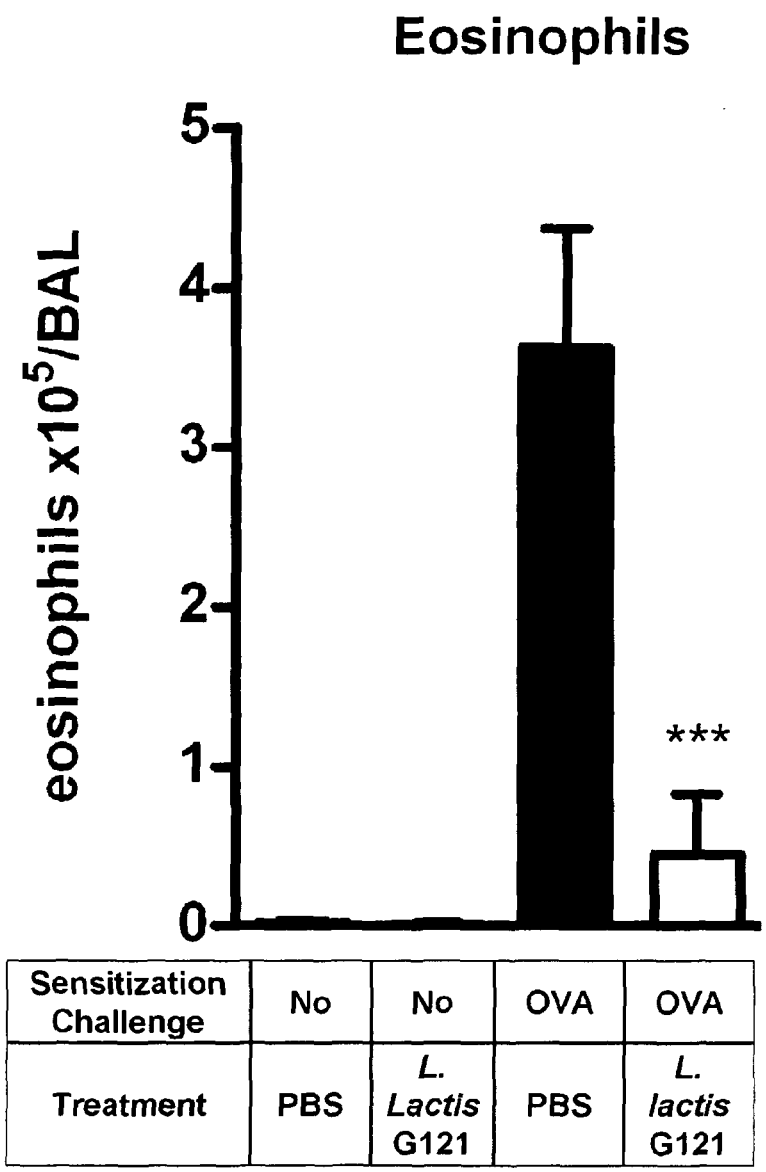
Figure 10:
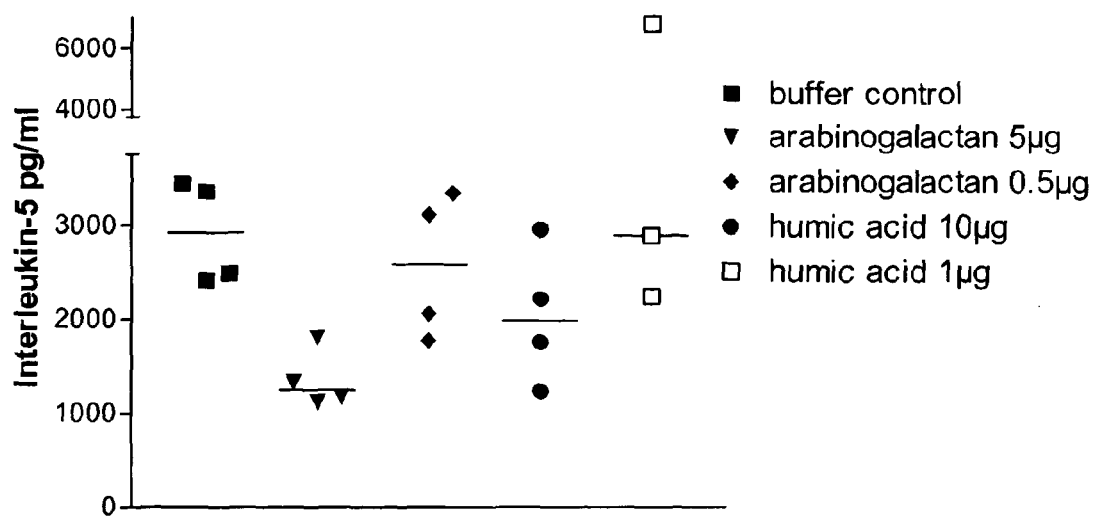

Treatment with either arabinogalactan or humic acid dose dependently reduced airway inflammation as measured by enumeration of eosinophilic granulocytes in broncho-alveolar lavage fluid (FIG. 8). Application of *Lactococcus lactis* lyophilized bacteria during sensitization shows a remarkable decrease of eosinophile invasion (FIG. 9). Moreover IL-5 production after restimulation with allergen was also reduced revealing that treatment with arabinogalactan acts on generation of Th2 lymphocytes (FIG. 10).

2.3. Determination of OVA Specific Antibodies of Isotypes IgE and IgG1

Figure 11:
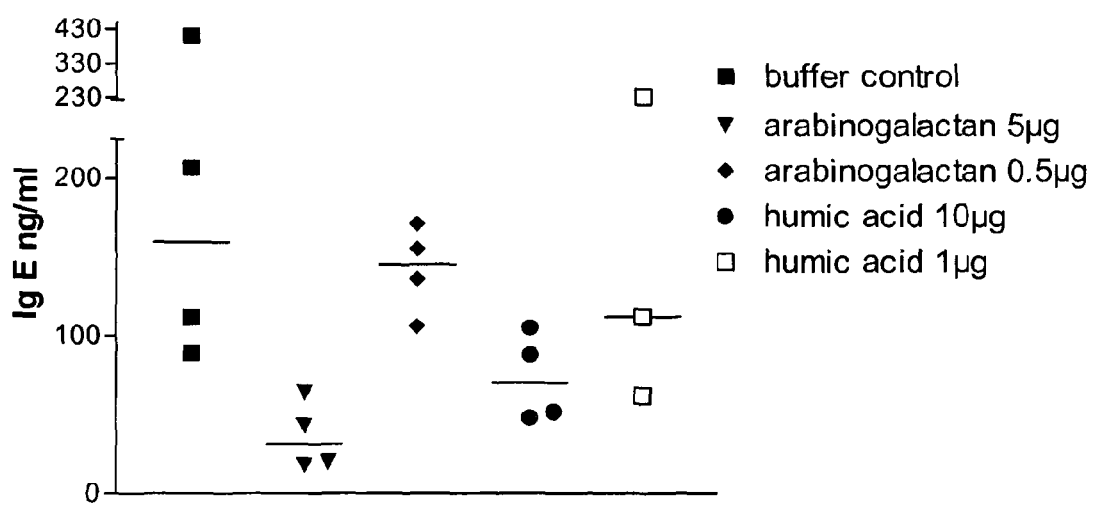

Since one major characteristic of atopic disease is production of IgE said IgE production was measured in mice that were treated with arabinogalactan or humic acid or *Lactococcus lactis* during sensitization (FIG. 11).

Treatment with 5 μg arabinogalactan during sensitization leads to significant reduction of IgE production in the airway lumen. Likewise treatment with humic acid results in dose dependent reduction of local IgE production. However, as already observed for eosinophilia and IL-5 production arabinogalactan exhibits much stronger effects on IgE titers than humic acid.

Figure 12:
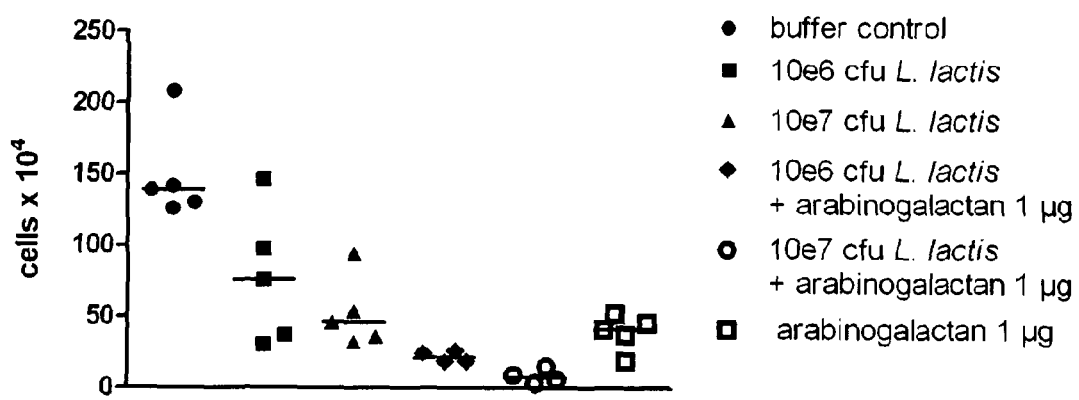
Figure 13:
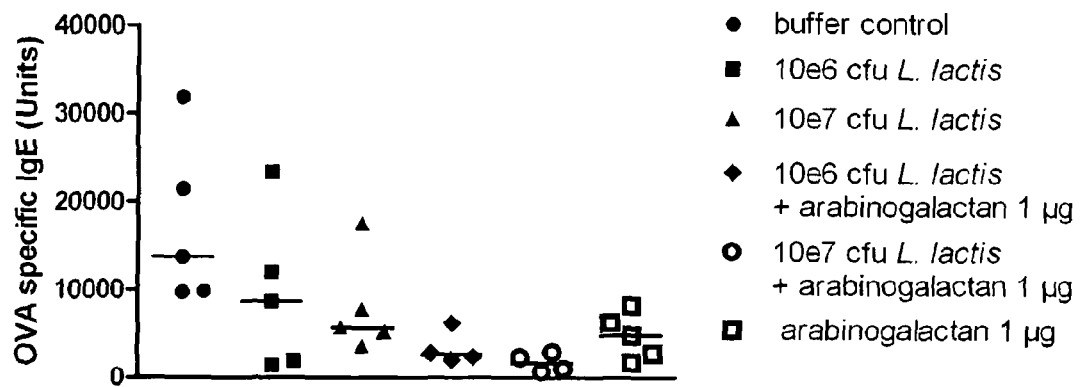

2.4 Synergistic Effects of a Combination of Arabinogalactan and *Lactococcus lactis* on the Cellular Composition of BAL and OVA Specific IgE Antibodies To demonstrate the synergistic effects of a combination of arabinogalactan and *Lactococcus* bacteria mice were treated with a submaximal dose ($10^6$ or $10^7$ cfu) of *Lactococcus lactis* in combination with a submaximal dose (1 μg) of arabinogalactan from Meadow foxtail (*Alopecurus pratensis*) according to the protocol shown in FIG. 7 and the description in examples 2.2 and 2.3. As shown in Table 2 as well as FIG. 12 and FIG. 13, respectively, the combination resulted in less eosinophilic granulocytes (FIG. 12) and less OVA specific IgE (FIG. 13) in the bronchoalveolar lavage of treated mice compared to accordant controls.

TABLE 2

Median values of eosinophilic cells and OVA specific antibodies in mice treated with arabinogalactan, different amounts of *L. lactis* or a combination of arabinogalactan and *L. lactis*, given in absolute numbers and relative to the buffer control (%):

|  | eosinophilic cells × $10^4$ | OVA specific IgE (units) |
|---|---|---|
| buffer control | 139.1 (100%) | 13,703 (100%) |
| $10^6$ cfu *L. lactis* | 76.1 (55%) | 8,624 (63%) |
| $10^7$ cfu *L. lactis* | 45.9 (33%) | 5,648 (41%) |
| $10^6$ cfu *L. lactis* + arabinogalactan 1 μg | 21.4 (15%) | 2,602 (19%) |
| $10^7$ cfu *L. lactis* + arabinogalactan 1 μg | 7.7 (6%) | 1,710 (13%) |
| arabinogalactan 1 μg | 41.4 (30%) | 4,813 (35%) |

Figure 14:
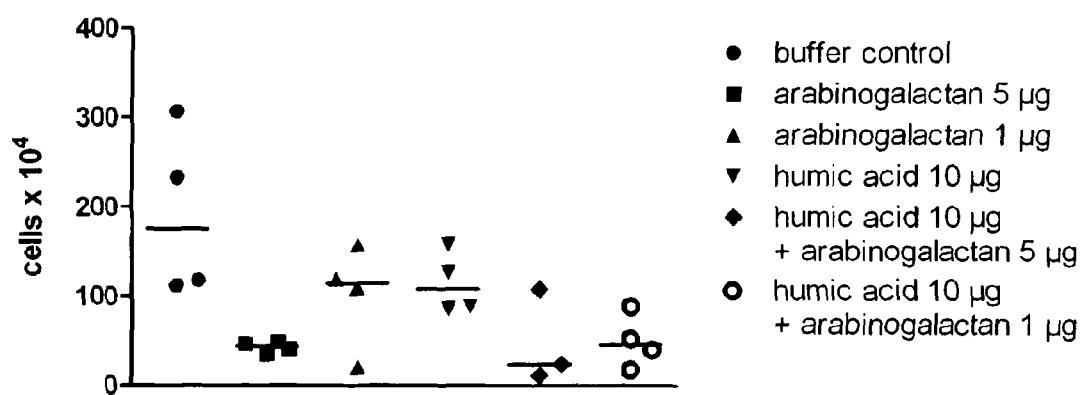
Figure 15:
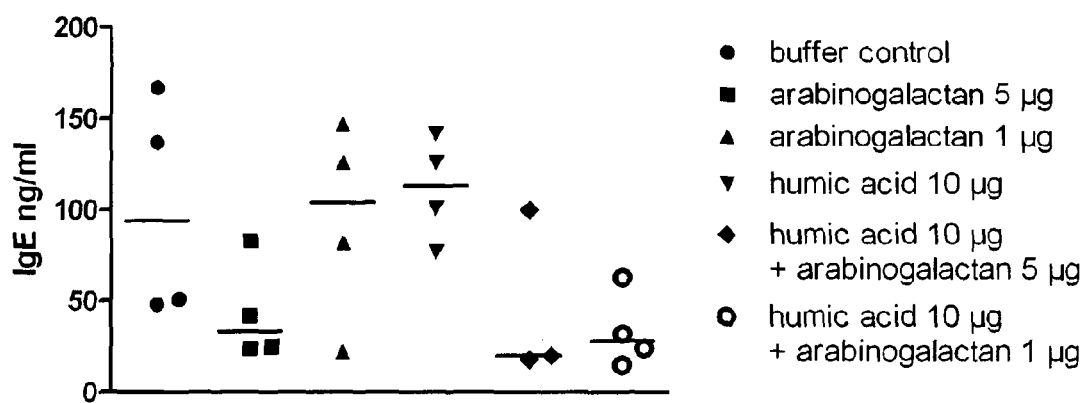

2.5 Synergistic Effects of a Combination of Arabinogalactan and Humic Acid on the Cellular Composition of BAL and Total IgE Antibodies To demonstrate the synergistic effects of a combination of arabinogalactan and humic acid mice were treated with 1 μg or 5 μg arabinogalactan from Meadow foxtail (*Alopecurus pratensis*) and 10 μg humic acid simultaneously according to the protocol shown in FIG. 7 and the description in examples 2.2 and 2.3. As shown in Table 3 as well as FIG. 14 and FIG. 15 respectively, the combination resulted in less eosinophilic granulocytes (FIG. 14) and less total IgE (FIG. 15) in the bronchoalveolar lavage of treated mice compared to controls.

TABLE 3

Median values of eosinophilic cells and total IgE antibodies in mice treated with different amounts of arabinogalactan, humic acid or a combination of arabinogalactan and humic acid, given in absolute numbers and relative to the buffer control (%):

|  | eosinophilic cells × $10^4$ | IgE (ng/ml) |
|---|---|---|
| buffer control | 175.9 (100%) | 94.0 (100%) |
| arabinogalactan 5 μg | 44.2 (25%) | 33.5 (36%) |
| arabinogalactan 1 μg | 114.5 (65%) | 104.0 (111%) |
| humic acid 10 μg | 108.1 (62%) | 113.5 (121%) |
| humic acid 10 μg + arabinogalactan 5 μg | 23.7 (14%) | 20.0 (21%) |
| humic acid 10 μg + arabinogalactan 1 μg | 46.5 (26%) | 28.0 (30%) |

2.6 Comparison of the Effects of Arabinogalactans from Different Sources

Figure 16:
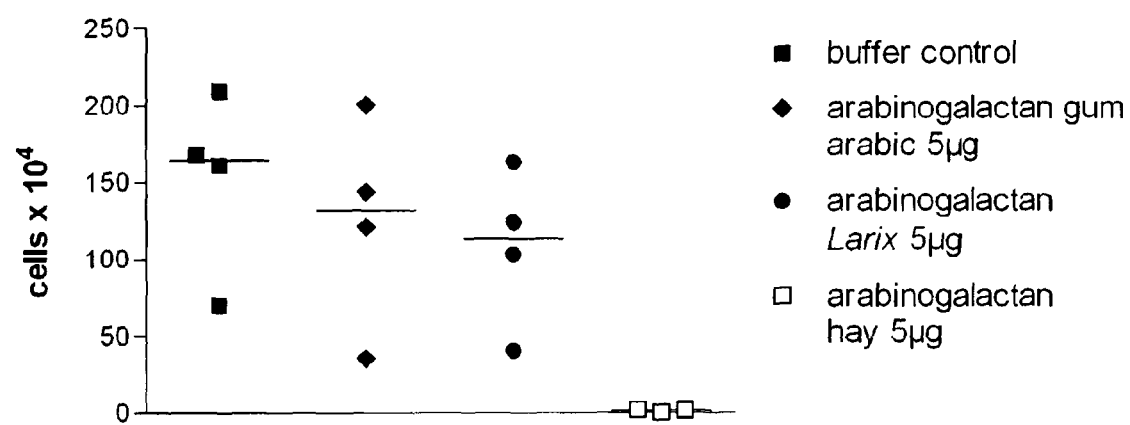
Figure 17:
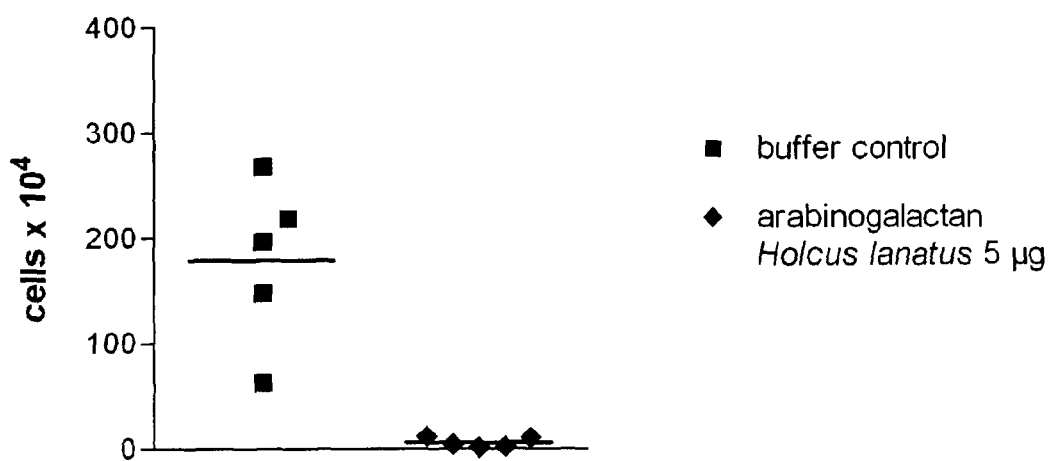

In addition to the experiments with arabinogalactan from Meadow Foxtail (*Alopecurus pratensis*) mice were also treated with 5 μg arabinogalactan from gum arabic, larch (*Larix*), hay or Yorkshire Fog (*Holcus lanatus*), respectively, in order to compare the effects of arabinogalactans from different sources. Experiments were conducted according to the protocol shown in FIG. 7 and the description in example 2.2. As shown in Table 4 and FIGS. 16 and 17 arabinogalactans isolated from hay or grass species reduced the number of eosinophilic granulocytes considerably more than the arabinogalactans isolated from other plants.

TABLE 4

Median values of eosinophilic cells in mice treated with arabinogalactans from different sources, given relative to the buffer control (%):

|   | eosinophilic cells |
|---|---|
| buffer control | 100% |
| arabinogalactan gum arabic 5 μg | 81% |
| arabinogalactan larch 5 μg | 71% |
| arabinogalactan hay 5 μg | 1% |
| arabinogalactan Yorkshire Fog 5 μg | 2% |
| arabinogalactan Meadow Foxtail 5 μg | 25% |

What is claimed is:

1. A method of treating an allergic disease comprising:
   initially administering an antiallergenic composition comprising at least one arabinogalactan or arabinogalactan protein into a mammal that is in need of such treatment prior to onset of symptoms of the allergic disease, and
   administering subsequent doses of said antiallergenic composition to said mammal,
   wherein said at least one arabinogalactan or arabinogalactan protein is isolated from at least one grass species or corresponds in its structural arrangement to an arabinogalactan isolatable from at least one grass species,
   wherein the allergic disease is selected from the group consisting of IgE-dependent Type I allergic diseases, and
   wherein the mammal has an increased risk to develop the allergic diseases relative to the general population based on diagnostic criteria.

2. The method according to claim 1, wherein the method is configured to treat one or more selected from the group consisting of hay fever, food allergy, asthma, urticaria, neurodermitis, and atopic dermatitis.

3. The method according to claim 1, wherein the method is configured to treat one or more selected from the group consisting of hay fever and asthma.

4. The method according to claim 1, wherein the at least one grass is selected from the group consisting of Meadow Foxtail (*Alopecurus pratensis*), timothy grass and timothy grass pollen (*Phleum pratense* L), Cock's Foot (*Dactylis glomerata*), Yorkshire Fog (*Holcus lannatus*), English Raygrass (*Lolium perenne*), Smooth Meadow grass (*Poa pratense*), Rye (*Secale cereale*) or grasses from related species and a mixture thereof.

5. The method according to claim 1, wherein the composition comprises an arabinogalactan selected from the group consisting of compounds of the structure shown in FIG. 1.

6. The method according to claim 1, wherein the composition comprises at least one further active ingredient selected from the group consisting of naturally occurring, isolated bacteria of the genus *Lactococcus* or fragments of said bacteria.

7. The method according to claim 6, wherein the bacteria are selected from the group consisting of strains of *Lactococcus lactis*.

8. The method according to claim 1, wherein the composition comprises at least one further active ingredient comprising humic acid.

9. The method according to claim 1, wherein the composition is a pharmaceutical composition in form of an aerosol, aqueous solution, suspension, lyophilisate, or powder for nasal or inhalative application.

10. The method according to claim 1, wherein the composition is in form for nasal or inhalative administration.

11. The method according to claim 1, wherein the method is suitable for application for an infant (baby) or a pregnant woman, which due to a positive family anamnesis has an increased risk to develop any allergic disease.

12. The method according to claim 1, wherein the method is suitable for application to a pregnant woman such that said treatment of an infant will be obtained by the application of the composition to the pregnant mother.

13. The method according to claim 1, wherein the method is suitable for application to an infant.

14. The method according to claim 1, wherein the composition is administered to a child directly after birth thereof.

15. The method according to claim 1, wherein the method is suitable for application to a child during the first years of the child's life up to 8-10 years.

16. The method according to claim 1, wherein the method is suitable for application to a child within the first five years of the child's life.

17. The method according to claim 1, wherein the method is suitable for application to a child within the first two years of the child's life.

* * * * *